United States Patent
Wayne et al.

(10) Patent No.: US 9,060,790 B2
(45) Date of Patent: Jun. 23, 2015

(54) TIBIOTALAR ARTHRODESIS GUIDE

(75) Inventors: Jennifer S. Wayne, Chesterfield, VA (US); Hieu T. Ta, Potomac Falls, VA (US); Bradley W. Zentgraf, Chesterfield, VA (US); Robert S. Adelaar, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 383 days.

(21) Appl. No.: 13/640,139

(22) PCT Filed: Apr. 15, 2011

(86) PCT No.: PCT/US2011/032605
§ 371 (c)(1),
(2), (4) Date: Oct. 9, 2012

(87) PCT Pub. No.: WO2011/133407
PCT Pub. Date: Oct. 27, 2011

(65) Prior Publication Data
US 2013/0030446 A1 Jan. 31, 2013

Related U.S. Application Data

(60) Provisional application No. 61/325,999, filed on Apr. 20, 2010.

(51) Int. Cl.
*A61B 17/60* (2006.01)
*A61B 17/17* (2006.01)
*A61B 17/86* (2006.01)

(52) U.S. Cl.
CPC ............. *A61B 17/1739* (2013.01); *A61B 17/60* (2013.01); *A61B 17/864* (2013.01); *A61B 2017/1775* (2013.01)

(58) Field of Classification Search
CPC ............................ A61B 17/17; A61B 17/1717
USPC ............................................. 606/96–98, 104
See application file for complete search history.

(56) References Cited

U.S. PATENT DOCUMENTS

| 4,722,331 A * | 2/1988 | Fox ................................. 606/96 |
| 5,228,459 A * | 7/1993 | Caspari et al. ................. 128/898 |
| 7,534,246 B2 * | 5/2009 | Reiley et al. ..................... 606/96 |
| 2003/0097131 A1 | 5/2003 | Schon et al. |

(Continued)

*Primary Examiner* — Anu Ramana
(74) *Attorney, Agent, or Firm* — Whitham Curtis Christofferson & Cook, PC (57) ABSTRACT

A Tibiotalar Arthrodesis Guide (TAG) used for fusion of the talus to the tibia is comprised of several basic components. The main component is a straight guide post upon which other components can slide. A curved arm is featured at the end of the straight guide post, featuring points at the ends which serve as indicators of the pins' exit sites based upon the lines of action of the parallel pins. The parallel guide cylinders are positioned on a movable arm which translates superiorly and inferiorly on the guide post of the handle, allowing a surgeon to adjust the device for varying ankle sizes. A "home-run" pin guide cylinder for a home-run guide pin is oriented superiorly and at an angle to the parallel guide cylinders. Using a similar concept as the parallel guide cylinders, the "home-run" guide is also attached to a movable arm that can translate inferiorly and superiorly along the main guide post. A medial guide cylinder for a medial guide pin passes through one of a plurality of holes in a vertical guide arm. The surgeon has the flexibility to utilize either the "home-run" or medial pins, depending on the needs of the patient and preference of the surgeon and, in either case, the "home-run" and medial pin pass between the two parallel pins.

15 Claims, 13 Drawing Sheets

(56) References Cited

U.S. PATENT DOCUMENTS

2006/0142870 A1* 6/2006 Robinson et al. .......... 623/21.18
2009/0062796 A1 3/2009 Parks et al.
2009/0099571 A1 4/2009 Cresina et al.
2009/0149861 A1 6/2009 Brodsky et al.

* cited by examiner

TIBIOTALAR ARTHRODESIS GUIDE

CROSS REFERENCE TO RELATED APPLICATION

This application claims priority to U.S. Provisional Application Ser. No. 61/325,999 filed Apr. 20, 2010.

BACKGROUND OF THE INVENTION

1. Field of the Invention

The present invention generally relates to orthopedic devices and, more particularly, to a Tibiotalar Arthrodesis Guide (TAG) used for fusion of the tibia to the talus.

2. Background Description

Arthrodesis is the artificial induction of joint ossification between two bones via surgery. This is done to relieve intractable pain in a joint which cannot be managed by pain medication, splints, or other normally-indicated treatments. The typical causes of such pain are fractures which disrupt the joint, and arthritis. It is most commonly performed on joints in the spine, hand, ankle, and foot. The goal of arthrodesis is to provide pain relief, restore skeletal stability, and improve alignment.

Fracture-dislocation of the talus is one of the most severe injuries of the ankle. Traumatic injury to the ankle and hindfoot often results in tibiotalar or subtalar arthritis. The associated joint pain, stiffness, and deformity may be difficult to treat with conservative measures. For such problems, arthrodesis of the ankle or hindfoot joints is the mainstay of treatment.

What is needed is a repeatable and accurate way to place three screws in a stable pattern across the tibiotalar joint for ankle fusion.

The closest prior art to the present invention is the Anterior Cruciate Ligament (ACL) guide. This device guides the orientation of one drill hole for the placement of the tibial tunnel in an ACL reconstruction procedure, beginning from the medial anterior proximal tibia and exiting in the center of the tibial plateau. This tunnel is then used as the conduit for an ACL graft to enter the knee joint and restore the function of a torn ACL.

SUMMARY OF THE INVENTION

An exemplary embodiment of the present invention is to provide a physical device that guides the placement of screws for fusion of the tibia to the talus in the ankle and a method of using that device.

According to the invention, there is provided a Tibiotalar Arthrodesis Guide (TAG) which enables the orientation of three screws across the joint for superior stability without the screws interfering with each other. More particularly, the TAG device allows for accurate and repeatable insertion of three screws during an ankle arthrodesis, or ankle fusion, procedure. Based upon a variation of the Roger Mann procedure, two of these screws are to be inserted from the lateral aspect of the ankle joint while the third is chosen from one of two orientations. Initially, transfixing pins (sometimes referred to as "arthrodesis pins" or "guide pins") are used to determine the orientation of the screws, after which cannulated screws are routed over the pins for the secure fixation, and the pins are removed. Two of the screws are inserted parallel to each other with their general entry point at the inferior aspect of the lateral talus. The insertion angle can be determined by the surgeon, but it is recommended that an insertion angle of approximately 55° (with respect to the transverse plan of the foot) (e.g., ±5-10°) be used to avoid potential fracture of the medial malleolus. The third arthrodesis screw, may be either a "home-run" screw or a medial screw. The optimal end position of the "home-run" screw is within the talar neck, a portion of dense bone in the medial talus. The medial screw as the third screw is inserted into the tibia and its line of action passes from the medial tibia into the lateral talus. The TAG device ensures that the "home-run" screw or the medial screw successfully passes in between the two parallel screws without touching.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION

The TAG device is comprised of several basic components. The main component is a straight guide post upon which other components can slide. A curved arm at the end of the straight guide post features points at the ends which serve as indicators of the pins' exit sites based upon the lines of action of the parallel guide cylinders. The parallel guide cylinders are positioned on a movable arm which translates superiorly and inferiorly on the guide post of the handle, allowing a surgeon to adjust the device for varying ankle sizes. In the preferred embodiment, the TAG device has both "home-run" and medial guide pins, allowing the surgeon to choose one or the other. The success of the "home-run" pin or the medial pin is determined by its orientation with respect to the two parallel guide pins. The "home-run" pin guide cylinder is oriented superiorly and at an angle to the parallel guide cylinders to ideally position the "home-run" pin through the body of the talus into the talar neck from the mid-distal tibia. Using a similar concept as the parallel guide cylinders, the "home-run" guide cylinder is also attached to a movable arm that can translate inferiorly and superiorly along the main guide post. The medial pin guide cylinder is oriented in a plane bisecting the plane of the two parallel pins and is supported by an arm between the points on the curved arm.

In the following description, the embodiments are illustrated for use with the right ankle. It will be understood, however, that similar implementations as mirror images are used with the left ankle. The TAG can be used for either a right or left ankle with only the homerun screw movable arm (21 in FIG. 1) needing a right/left design; the medial arm (23 in FIG. 1) simply needs to be flipped on the guide post 11.

Figure 1:
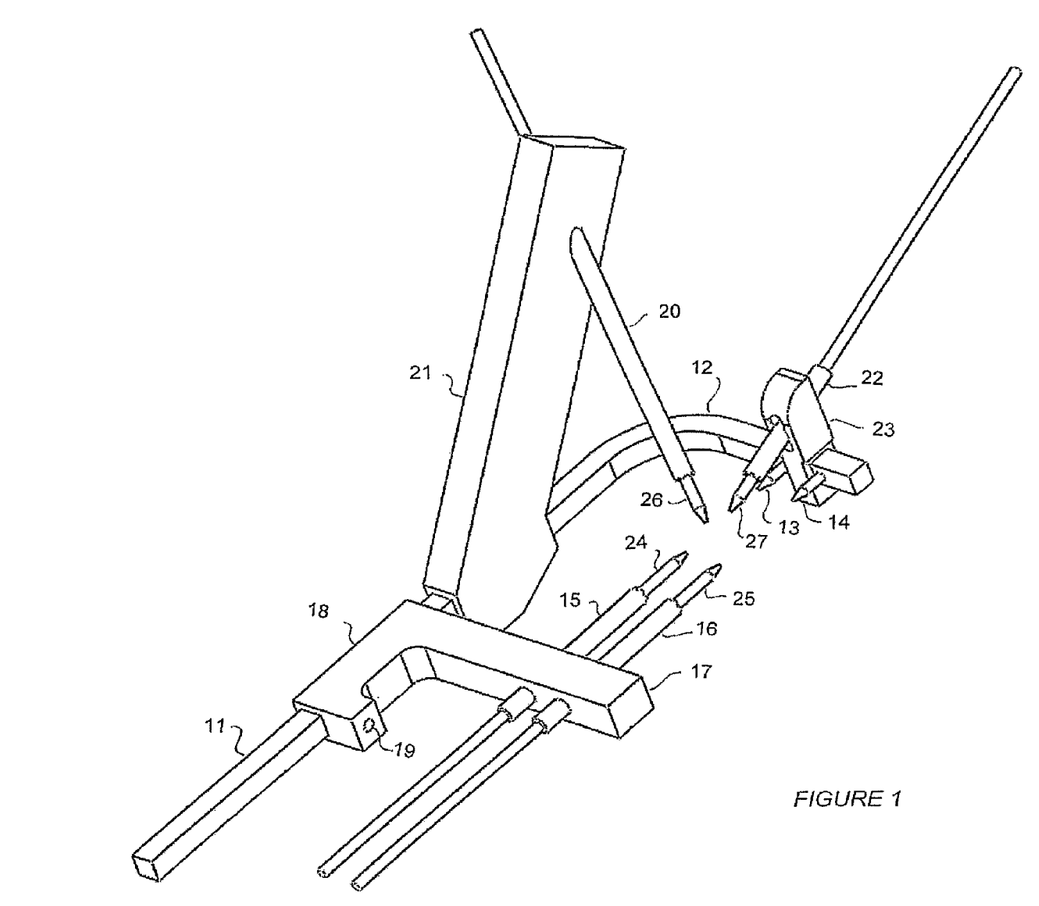
FIG. 1 is a perspective view of a first embodiment of the Tibiotalar Arthrodesis Guide (TAG) device according to the invention having both a "home-run" guide pin and a medial guide pin.
Figure 2:
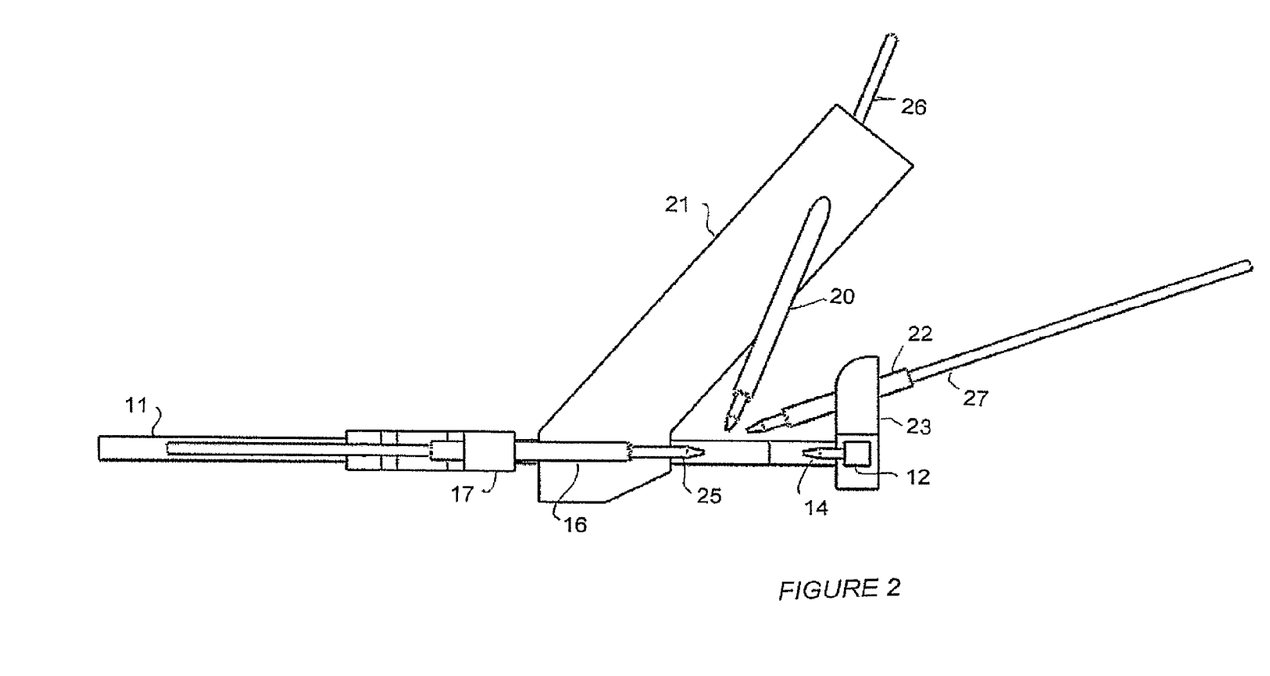
FIG. 2 is a side view of the TAG device embodiment of FIG. 1.
Figure 3:
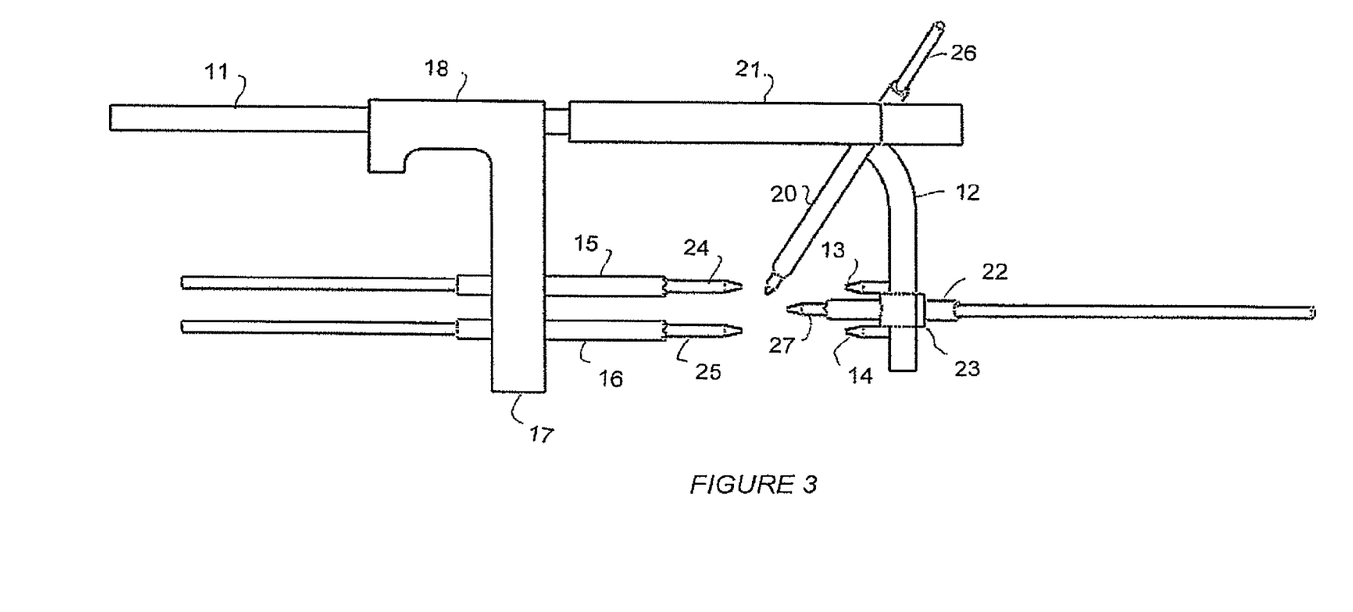
FIG. 3 is a top view of the TAG device embodiment of FIG. 1.

Referring now to the drawings, and more particularly to FIGS. 1 to 3, there are shown a perspective view, a side view and a top view, respectively, of a first embodiment TAG device. The device comprises a straight guide post 11 upon which other components can slide. The end of the guide post is formed as a curved arm 12 having a pair of points 13 and 14 which serve as indicators of parallel guide pin exit sites. Parallel pin guide cylinders 15 and 16 are held by an arm 17 which is perpendicular to the guide post 11. The distance between the parallel guide cylinders 15, 16 can be made adjustable to accommodate different size taluses, although there is a minimum distance that must be met in order for the oblique angled homerun screw 26 to fit in between. The arm 17, in turn, is fixed to or integral with a movable slide 18 which translates along the guide post 11 and can be secured by means of a set screw 19. Alternatively, a knob and screw can be used instead of a set screw, making the process of securing the movable slide 18 a process that can be accomplished by hand without the need for a tool. The adjustment of the movable slide 18 allows the surgeon to adjust the device for varying ankle sizes. The "home-run" pin guide cylinder 20 is oriented superiorly and at an angle to the parallel guide cylinders 15 and 16. The "home-run" pin guide cylinder 20 is attached to a movable arm 21 that can translate along the main guide post 11. The medial pin guide cylinder 22 passes through a hole in a vertical guide arm 23 which is positioned between the points 13 and 14. To allow flexibility in use, the medial pin guide cylinder may fit into one of, e.g., three holes (FIG. 1 shows three vertically aligned holes) in vertical guide arm 23 to permit different orientations. In either case, the "home-run" pin guide 20 or the medial pin guide cylinder 22 can be adjusted by the surgeon for varying ankle sizes.

The parallel pin guide cylinders 15 and 16 guide pins 24 and 25 which are inserted into the ankle first. This is done, for example, by attaching the guide pins 24 and 25 to a pneumatic drill and drilling the pins into the ankle. Once the two parallel guide pins 24 and 25 have been inserted into the ankle, a decision is made by the surgeon as to whether the "home-run" pin 26 in guide cylinder 20 or the medial pin 27 in the guide cylinder 22 is to be inserted into the ankle. Only one of these pins is inserted. In either case, the orientation of the respective guide cylinders is such that the corresponding pins are inserted between the parallel pins without touching those pins. Thus, the preferred embodiment of the TAG device features two options for insertion of either a "home-run" pin or a medial pin. Both options allow either the "home-run" screw or the medial screw to be positioned in between the two parallel pins. The guide cylinders for the guide pins can be made to different diameters to permit smaller guide pins, and thus smaller cannulated screws to be inserted. Hence, the TAG device might include a collection of different diameter guide pins and guide cylinders or a collection of guide pins with guide cylinders of adjustable diameters.

Figure 4:
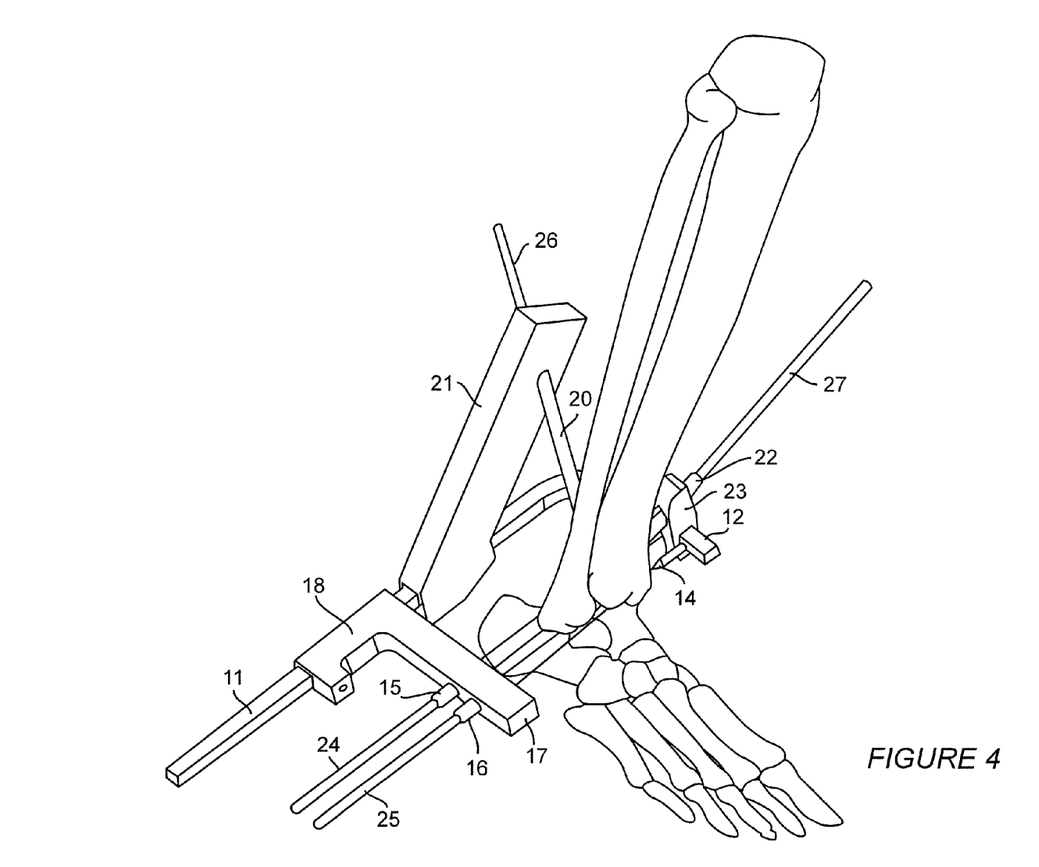
FIG. 4 is a perspective view, partially in overlay, of the TAG device embodiment of FIG. 1 on an orthopaedic model of the right lower leg and foot.

FIG. 4 is a perspective view showing the TAG device of the first embodiment attached to an orthopaedic model of a right lower leg and foot. In this illustration, the parallel guide pins 24 and 25 have been inserted into the ankle. The surgeon next determines which of the "home-run" pin or the medial pin is to be inserted. After insertion of the three pins, the guide cylinders are removed and cannulated screws are inserted over the pins. Thereafter, the guide pins are removed, leaving the three cannulated screws to complete the procedure for fusion of the talus to the tibia.

Figure 11:
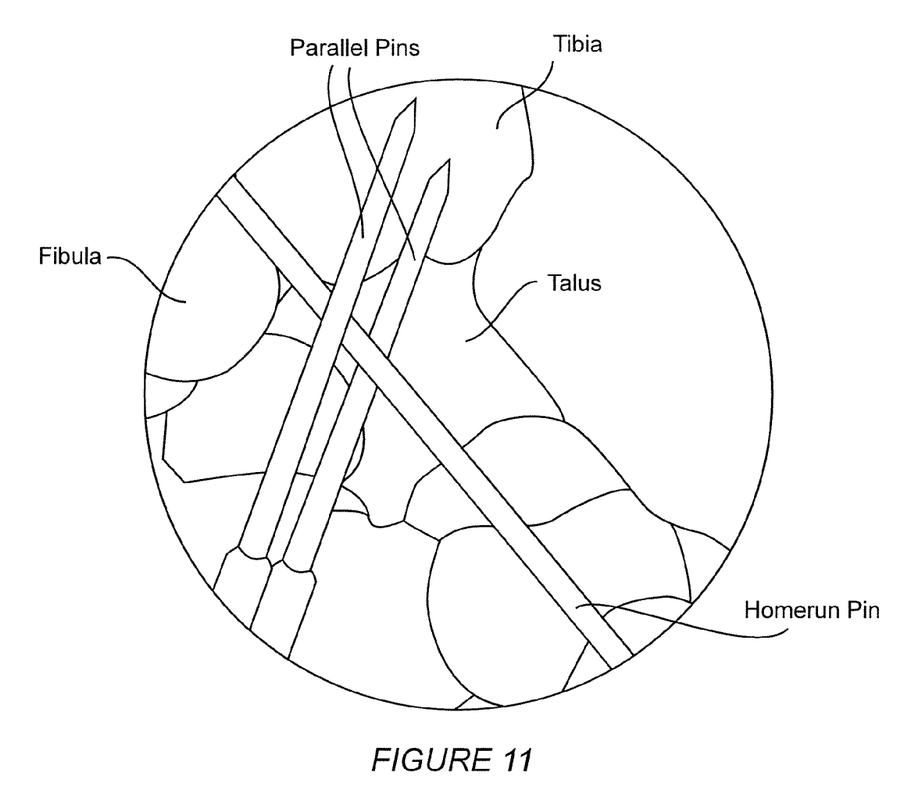
FIG. 11 is an X-ray image, oblique anterior view of the TAG with homerun guide pin.
Figure 12:
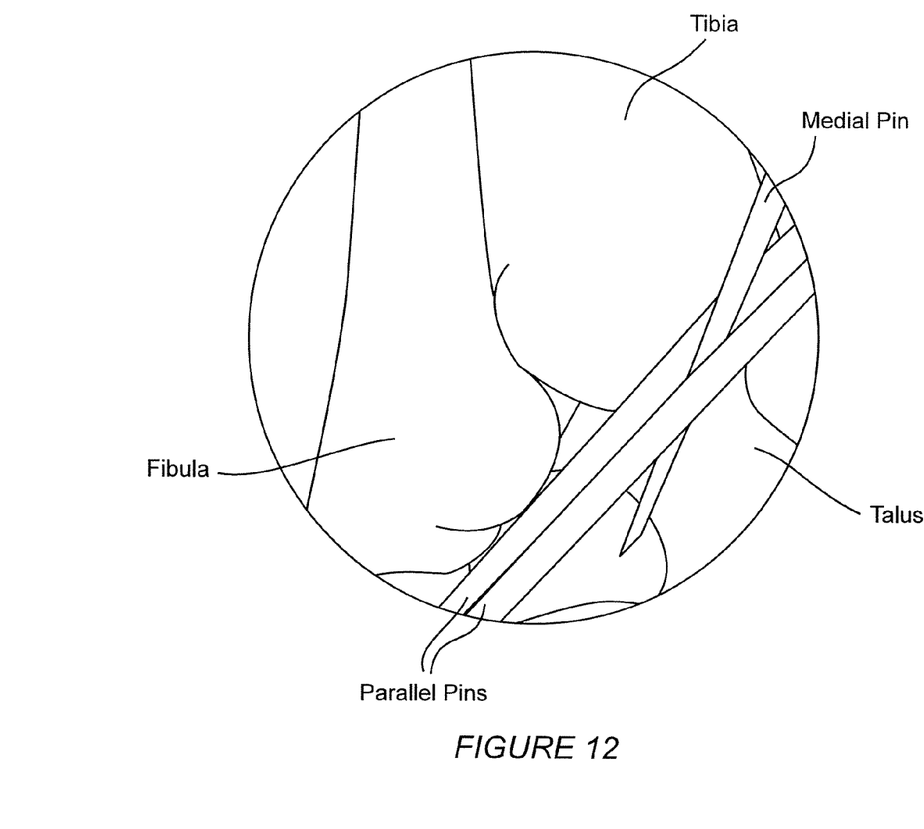
FIG. 12 is an X-ray image, lateral view, of the TAG with medial guide pin.
Figure 13:
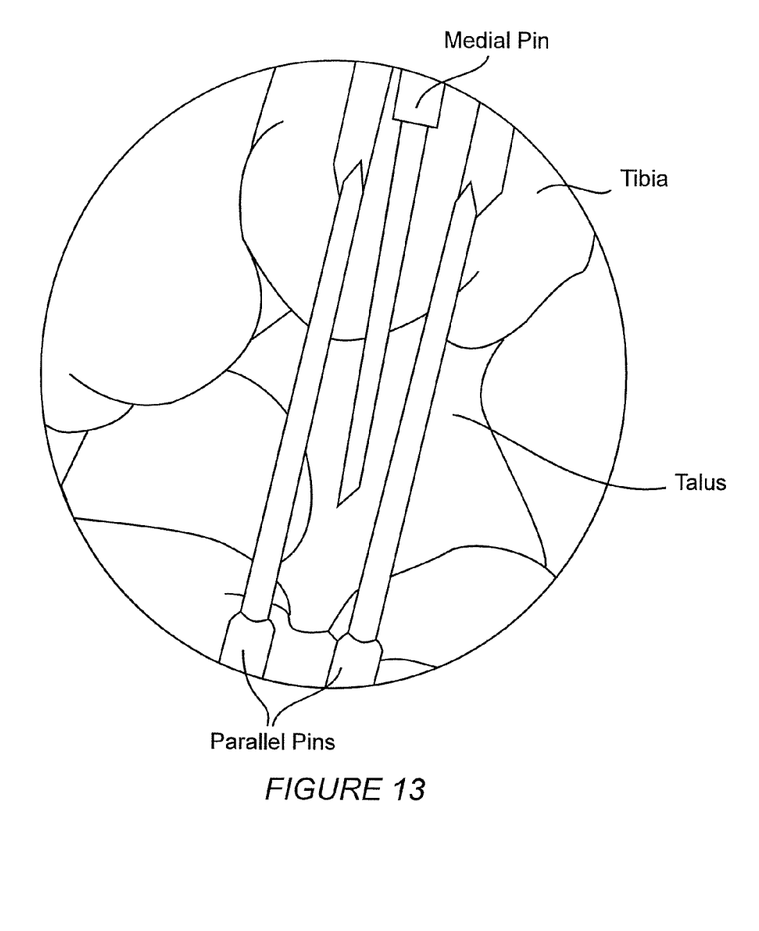
FIG. 13 is an X-ray image, anterior view close up, of the TAG with medial guide pin.

Use of the TAG device during an ankle arthrodesis procedure will potentially decrease the amount of X-ray exposure on surgeons and patients, decrease the overall length of the procedure, and increase the rate of joint fusion by improving the accuracy of screw placement. The TAG device would be utilized during an ankle arthrodesis in the following manner:

1. The TAG device would be positioned with the curved arm 12 medial to the ankle joint such that the parallel pin guide cylinders 15 and 16 are on the lateral side of the joint and either the "home-run" pin is in its proper position posterolateral with respect to the ankle joint, or the medial pin is in its proper position when it is medially on the joint.
2. The orientation of the parallel pins 24 and 25 is addressed first.
3. The surgeon positions the TAG device in the desired orientation such that ideal insertion angles are attained for individual patients.
4. The pin guide cylinders 15 and 16 for the parallel pins 24 and 25 are slid forward along the guide post 11 such that both the parallel pin guide cylinders 15 and 16 and exit site indicator points 13 and 14 are tightened against bone on the medial and lateral sides. The movable slide 18 is fixed to the guide post 11 by tightening the set screw 19 on the slide 18.
5. Once the parallel pin guide cylinders 15 and 16 are properly positioned, the guide cylinder 20 for the "home-run" pin or the guide cylinder 22 for the medial pin can then be positioned to be in contact with the bone.
6. The orientation of the guide cylinders 15, 16 and 20 or 22 should be re-evaluated before the pins are inserted to determine if the desired orientation has been achieved.
7. Once it is determined that the guide cylinders 15, 16 and 20 or 22 are in the desired position, the arthrodesis guide pins 24, 25 and 26 or 27 can be inserted into the ankle joint without fear of touching one another.
8. The parallel guide cylinders 15 and 16, as well as the arm 17, can then be removed from the straight guide post 11 (which functions as the main frame of the TAG device), and cannulated screws (not shown) are inserted into the ankle joint over top of the arthrodesis guide pins 24 and 25.
9. After the parallel cannulated screws have been inserted into the ankle joint, the arthrodesis guide pins 24 and 25 can be removed by backing them out of the screws.
10. Once the parallel screws have been placed, the entire device can be removed from the ankle, leaving only the "homerun" arthrodesis guide pin or medial pin for its cannulated screw to be inserted.
11. Once again, a cannulated screw (not shown) is inserted over top of the "home-run" pin 26 or the medial pin 27, whichever was used, at which point the pin is removed from the cannulated screw, leaving the three cannulated screws within the ankle joint in the desired orientation. See FIGS. 11-13 which show X-ray images of the TAG device with the medial screw in place (FIGS. 11 and 12) and with the "home-run" screw in place (FIG. 13). In these images, the TAG device is made of an X-ray transparent material, such as a plastic or carbon fiber, to allow the X-ray images to be made. FIGS. 11-13 also show the two parallel screws in place.

Figure 5:
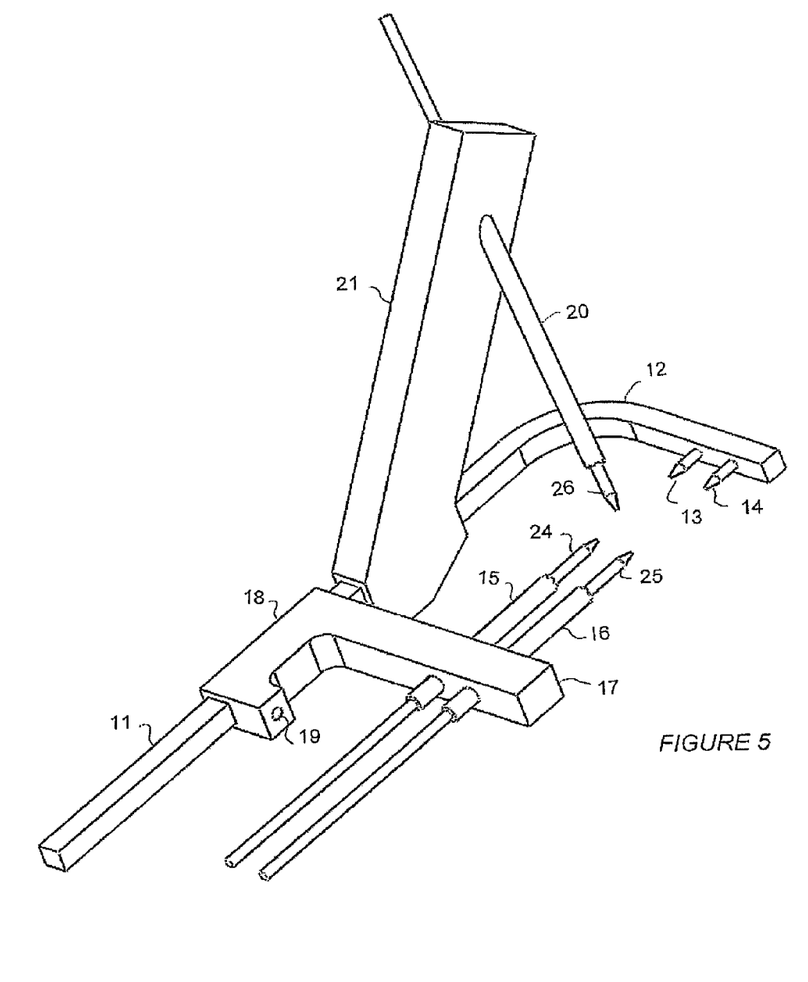
FIG. 5 is a perspective view of a second embodiment of the TAG device according to the invention having only a "home-run" guide pin.
Figure 6:
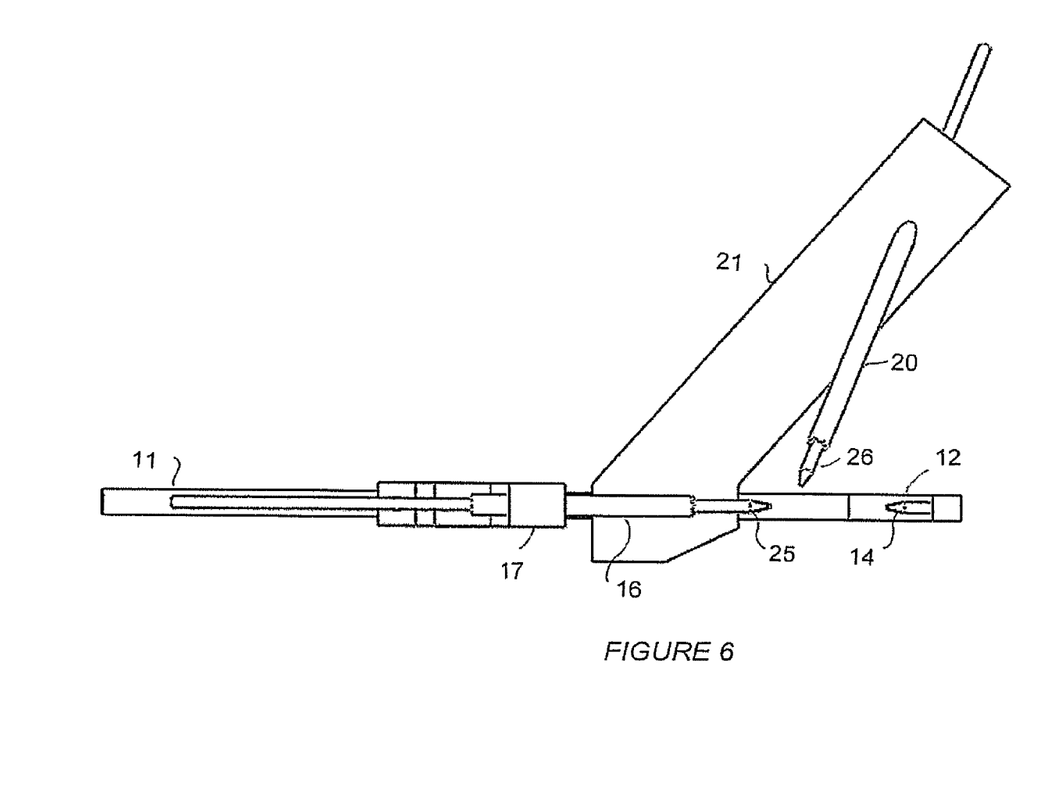
FIG. 6 is a side view of the TAG device embodiment of FIG. 5.
Figure 7:
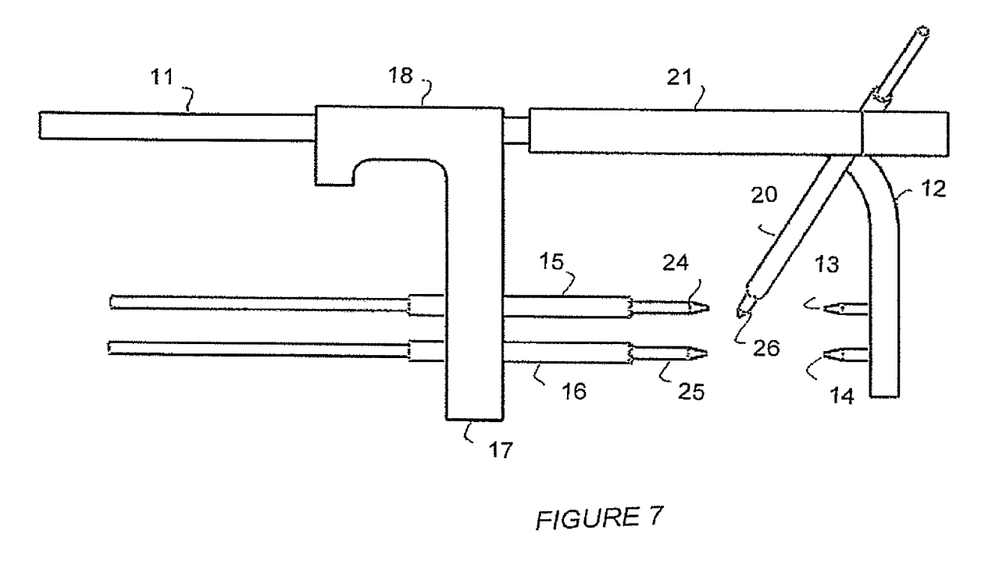
FIG. 7 is a top view of the TAG device embodiment of FIG. 5.
Figure 8:
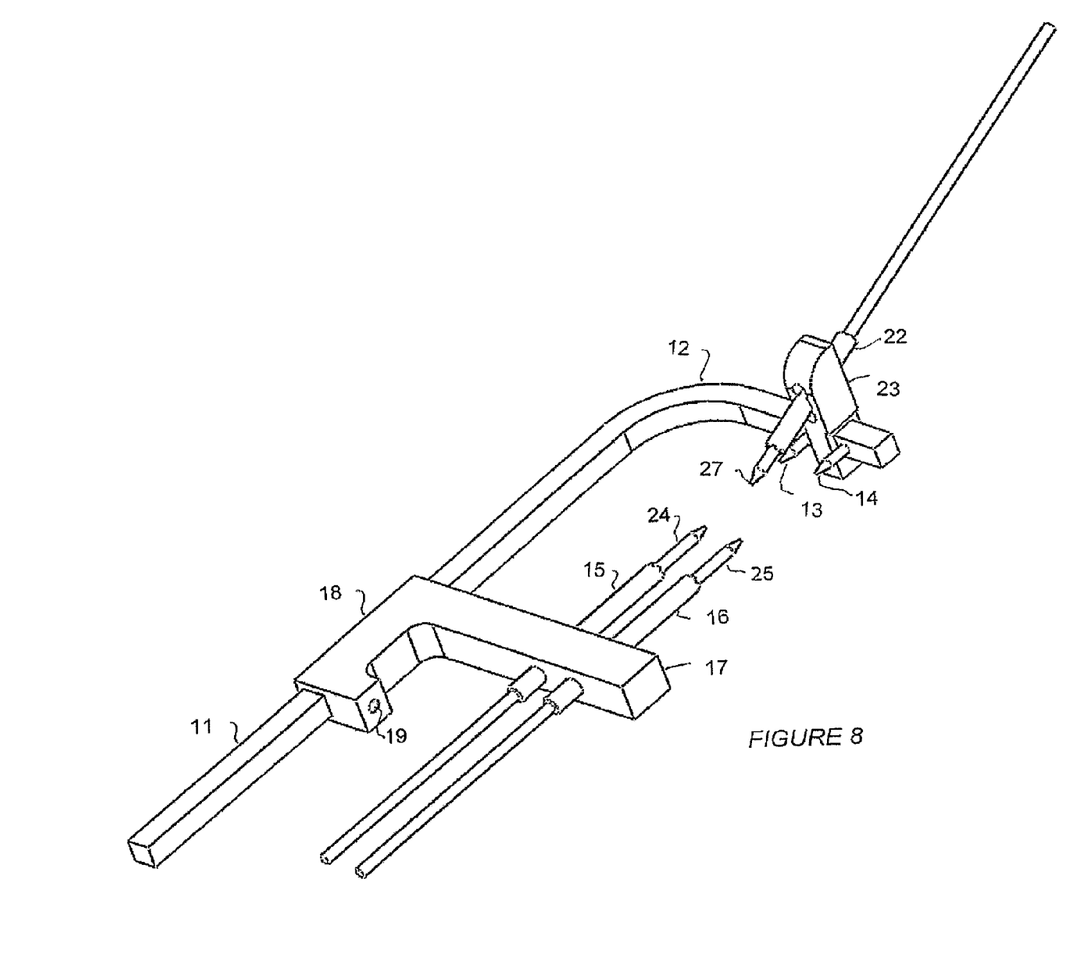
FIG. 8 is a perspective view of a third embodiment of the TAG device according to the invention having only a medial guide pin.
Figure 9:
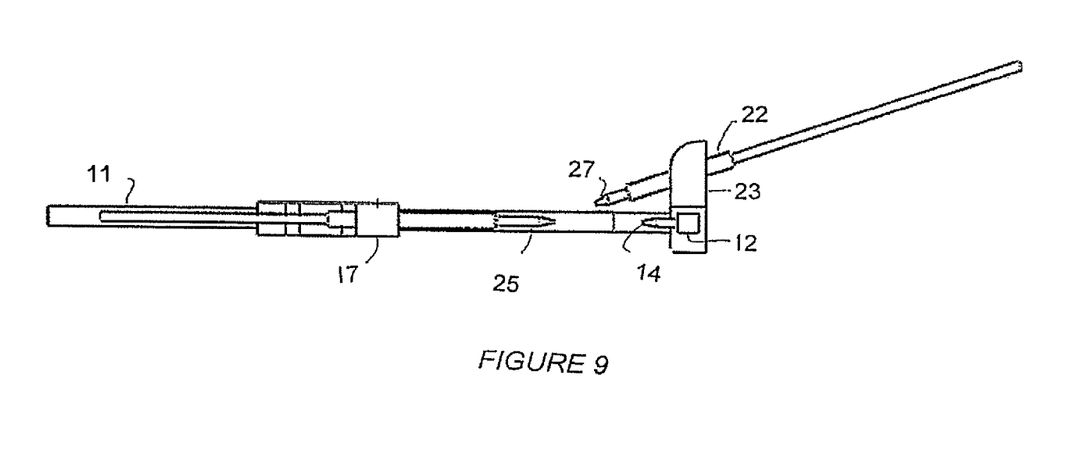
FIG. 9 is a side view of the TAG device embodiment of FIG. 8.
Figure 10:
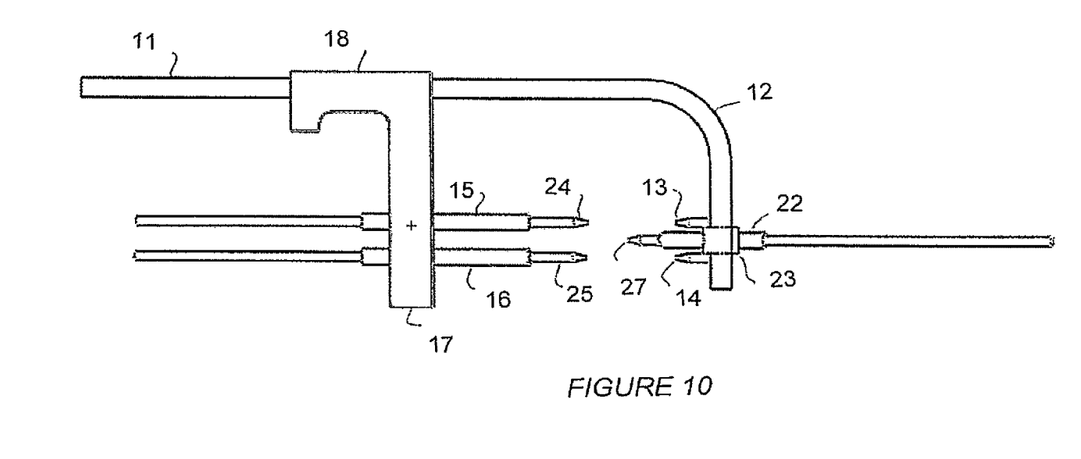
FIG. 10 is a top view of the TAG device embodiment of FIG. 8.

Simpler versions of the TAG device according to the invention can also be made. For example, the second embodiment shown in FIGS. 5, 6 and 7 omits the medial pin guide 22 cylinder and the vertical arm 23 positioned between the points 13 and 14. In this embodiment, only the "home-run" pin 26 can be inserted into the ankle. The third embodiment omits the "home-run" pin guide 20 and movable arm 21. In this embodiment, only the medial pin 27 can be inserted into the ankle.

While the invention has been described in terms of preferred embodiments, those skilled in the art will recognize that the invention can be practiced with modification within the spirit and scope of the appended claims.

Having thus described our invention, what we claim as new and desire to secure by Letters of Patent is a follows:

1. A Tibiotalar Arthrodesis Guide (TAG) device used for fusion of the talus to the tibia comprising:
   a straight guide post upon which other components can slide;
   a curved arm having a pair of points which serve as indicators of pin exit sites;
   first and second pin guide cylinders parallel to one another and held by an arm which is perpendicular to the straight guide post, the arm, in turn, being fixed to a movable slide which translates along the straight guide post, allowing a surgeon to adjust the device for varying ankle sizes;
   a third pin guide cylinder oriented at an angle with respect to the first and second pin guide cylinders such that first and second pins inserted into each of the first and second pin guide cylinders and a third pin inserted into the third pin guide cylinder do not touch one another when inserted into the ankle,
   whereby the TAG device ensures that a screw successfully inserted with the aid of the third pin passes in between two parallel screws previously inserted with the aid of the first and second pins without touching the two parallel screws, enabling the orientation of three screws across the joint for superior stability without interfering with each other.

2. The TAG device of claim 1, wherein the third pin guide cylinder is a "home-run" pin guide cylinder oriented superiorly and at an angle to the first and second pin guide cylinders, and further comprising a movable arm that can translate along the straight guide post, the "home-run" pin guide cylinder being attached to the movable arm.

3. The TAG device of claim 1, wherein the third pin guide cylinder is a medial pin guide cylinder oriented superiorly and in a plane bisecting a plane of the first and second pin guide cylinders, and further comprising a vertical guide arm positioned between the pair of points on the curved arm, the medial pin guide cylinder being attached to the vertical guide arm.

4. The TAG device of claim 1, wherein the third pin guide cylinder is a "home-run" pin guide cylinder oriented superiorly and at an angle to the first and second pin guide cylinders, and further comprising:
   a movable arm that can translate along the straight guide post, the "home-run" pin guide cylinder being attached to the movable arm;
   a fourth pin guide cylinder which is a medial pin guide cylinder oriented superiorly and in a plane bisecting a plane of the first and second pin guide cylinders; and
   a vertical guide arm positioned between the pair of points on the curved arm, the fourth pin guide cylinder being attached to the vertical guide arm.

5. The TAG device of claim 1, further comprising means for securing a movable slide once the device has been adjusted for a specific ankle size.

6. The TAG device of claim 5, wherein the means of securing the movable slide is a set screw.

7. The TAG device of claim 5, wherein the means of securing the movable slide is a fixing knob.

8. A method of performing an ankle arthrodesis using a Tibiotalar Arthrodesis Guide (TAG) device comprised of a straight guide post upon which other components can slide, a curved arm having a pair of points which serve as indicators of pin exit sites, first and second pin guide cylinders parallel to one another and held by an arm which is perpendicular to the straight guide post, the arm, in turn, being fixed to a movable slide which translates along the straight guide post and can be secured allowing a surgeon to adjust the device for varying ankle sizes, a third pin guide cylinder oriented at an angle with respect to the first and second pin guide cylinders such that first and second arthrodesis guide pins inserted into each of the first and second pin guide cylinders and a third arthrodesis guide pin inserted into the third pin guide cylinder do not touch one another when inserted into the ankle, the method comprising the steps of:
   positioning the TAG device with the curved arm medial to the ankle joint such that the first and second pin guide cylinders are on a lateral side of the joint and the third pin guide cylinder is at an angle to the first and second pin guide cylinders with respect to the ankle joint;
   sliding the first and second pin guide cylinders for the first and second arthrodesis guide pins forward along the straight guide post such that both the first and second pin guide cylinders and exit site indicator points are tightened against bone;
   once the first and second pin guide cylinders are properly positioned, sliding the third pin guide cylinder through a hole in a movable arm or vertical guide arm so that the third guide cylinder is in contact with bone;
   inserting the first and second arthrodesis guide pins into the ankle joint with the aid of the first and second pin guide cylinders and then inserting the third arthrodesis guide pin into the ankle joint with the aid of the third pin guide cylinder;
   removing the first and second pin guide cylinders from the straight guide post, and inserting two parallel cannulated screws into the ankle joint over top of the first and second arthrodesis guide pins;
   after the two parallel cannulated screws have been inserted into the ankle joint, removing the first and second arthrodesis guide pins by backing them out of the two parallel cannulated screws so that only the two parallel cannulated screws remain within the ankle joint;
   once the two parallel cannulated screws have been placed, removing the third pin guide cylinder; and
   inserting a third cannulated screw over top of the third arthrodesis guide pin, and removing the third arthrodesis guide pin from the third cannulated screw, leaving the three cannulated screws within the ankle joint in the desired orientation,
   whereby the third cannulated screw inserted with the aid of the third arthrodesis guide pin passes in between the two parallel cannulated screws previously inserted with the aid of the first and second arthrodesis guide pins without touching the two parallel cannulated screws enabling the orientation of three cannulated screws across the joint for superior stability without interfering with each other.

9. The method of performing an ankle arthrodesis of claim 8, wherein the third pin guide cylinder is a "home-run" pin guide cylinder which is oriented superiorly and at an angle to the first and second pin guide cylinders.

10. The method of performing an ankle arthrodesis of claim 8, wherein the third pin guide cylinder is a medial pin guide cylinder which passes through a hole in a vertical guide arm positioned between the pair of points and wherein the third arthrodesis pin is a medial arthrodesis guide pin.

11. The method of performing an ankle arthrodesis of claim 10, wherein the hole through which the third pin guide cylinder passes is selected from amongst a plurality of holes in said vertical guide arm in order to permit adjustment of orientation of said medial arthrodesis guide pin.

12. The method of performing an ankle arthrodesis of claim 8, further comprising the step of fixing the movable slide to the straight guide post.

13. The method of performing an ankle arthrodesis of claim 12, wherein the step of fixing the movable slide is performed by tightening a set screw on the movable slide.

14. The method of performing an ankle arthrodesis of claim 12, wherein the step of fixing the movable slide is performed by tightening a fixing knob and screw on the movable slide.

15. The method of performing an ankle arthrodesis of claim 8, further comprising the step of re-evaluating the orientation of one or more of the first, second, and third pin guide cylinders before the first, second, and third arthrodesis guide pins are inserted to determine if the desired orientation has been achieved, and once it is determined that the one or more of the first, second, and third pin guide cylinders are in the desired position, inserting the first, second, and third arthrodesis guide pins into the ankle joint.

* * * * *